United States Patent [19]

Bonse et al.

[11] Patent Number: 4,496,736

[45] Date of Patent: Jan. 29, 1985

[54] PROCESS FOR THE PREPARATION OF CARBOXYLIC ACIDS AND N-TERT.-ALKYLAMINES

[75] Inventors: Gerhard Bonse; Gerhard Marzolph, both of Cologne; Heinz U. Blank, Odenthal, all of Fed. Rep. of Germany

[73] Assignee: Bayer Aktiengesellschaft, Leverkusen, Fed. Rep. of Germany

[21] Appl. No.: 384,470

[22] Filed: Jun. 3, 1982

[30] Foreign Application Priority Data

Jun. 23, 1981 [DE] Fed. Rep. of Germany ....... 3124652
Mar. 27, 1982 [DE] Fed. Rep. of Germany ....... 3211326

[51] Int. Cl.$^3$ .................. C07D 211/90; C07D 53/134
[52] U.S. Cl. .................................... 546/327; 546/319; 562/400; 562/490; 562/492; 562/493; 562/495; 562/496; 562/606; 564/1; 564/336; 564/462; 564/488
[58] Field of Search ............... 562/493, 496, 490, 492, 562/495; 546/319, 327; 564/336, 462, 488, 1

[56] References Cited

U.S. PATENT DOCUMENTS 3,898,280  8/1975  Pander ............................... 564/488

FOREIGN PATENT DOCUMENTS 2164239  7/1972  Fed. Rep. of Germany .
50-95210  7/1975  Japan .

OTHER PUBLICATIONS

Hutchison et al., Australian J. of Chem. 18(5), pp. 699–706, (1965).
Ritter et al., J. A. C S., vol. 70, (1948), pp. 4045–4050.

Primary Examiner—Henry R. Jiles
Assistant Examiner—Bernard I. Dentz
Attorney, Agent, or Firm—Sprung, Horn, Kramer & Woods

[57] ABSTRACT

Carboxylic acids and N-t.-alkylamines can be prepared simultaneously by the alkaline pressure hydrolysis of N-t.-alkyl carboxylic acid amides. A 5 to 50% strength by weight aqueous solution of an alkali metal hydroxide is employed for this purpose in an amount of 1.0 to 1.3 mols per mol of the amide. The process is carried out at 200° to 350° C.

19 Claims, No Drawings

PROCESS FOR THE PREPARATION OF CARBOXYLIC ACIDS AND N-TERT.-ALKYLAMINES

The present invention relates to a process for the simultaneous preparation of carboxylic acids and N-tert.-alkylamines by alkaline hydrolysis, under pressure, of N-tert.-alkylcarboxylic acid amides.

Carboxylic acids can be prepared by hydrolyzing the corresponding nitriles. Thus, for example, phenylacetic acid is prepared by alkaline or acid hydrolysis of benzyl cyanide (Ullmanns Enzyklopädie der technischen Chemie [Ullmann's Encyclopaedia of Industrial Chemistry], 4th edition, 1976, volume 11, page 71; Organic Syntheses, Coll. Vol. 1, 436). In these hydrolysis processes the nitrogen of the nitrile group is lost as ammonia or an ammonium salt.

N-t.-alkylamines can be prepared by hydrolyzing selected N-t.-alkylamides. Alkaline conditions of hydrolysis must be used for this purpose, since, under acid conditions, these amides split into an olefin, ammonia and a carboxylic acid (J. Am. Chem. Soc. 70 (1948), 4046).

However, the alkaline hydrolysis of N-tert.- alkylamides requires drastic reaction conditions. Thus U.S. Pat. No. 2,548,585 describes the hydrolysis of N-t.-butylurea or N,N'-di-t.-butylurea using at least 2 mols of NaOH per mol of starting material in ethoxyethanol as the solvent, the t.-butylamine which has been split off being removed directly from the reaction medium by distillation.

In J. Am. Chem. Soc. 70 (1948), 4048 it is stated that N-tert.-alkylformamides can be hydrolized, with liberation of the amine, by heating under reflux with 20–32% strenth NaOH. This process is also used in German Auslegeschrift [German Published Specification] 2,236,040 for the hydrolysis of N-tert.-alkylformamides.

In contrast, the hydrolysis of amides of higher carboxylic acids takes place with very much more difficulty. Thus Zabicki, in Chemistry of Amides, pages 824 et seq. (Interscience 1970), teaches that the rate of alkaline hydrolysis of amides is greatly retarded by branching at the α-C atom of the carboxylic acid radical. The effect of branching at the α-C atom of the amine radical is even greater. Thus the rate of hydrolysis in the case of acetamides falls to 1/18 in going from acetamide to N-methylacetamide, while the rate of hydrolysis of N-t.-butylacetamide was so low that it could not be determined.

Scholl, in Liebigs Annalen der Chemie 338, 16 (1905), also states that the hydrolysis of N-t.-butylacetamide requires very drastic conditions. According to J. Am. Chem. Soc. 70 (1948), 4048, the hydrolysis of N-t.-butylacetamide using KOH in glycol under reflux conditions (boiling point of glycol: 197° C.) can only be carried out with a 27% yield of t.-butylamine even after a reaction time of 48 hours.

Rumanian Patent Application No. 55,714 (quoted by C.A. 80, 107,972x) describes the hydrolysis of N-butylacetamide using potassium hydroxide in ethylene glycol.

The hydrolysis of N-t.-octylacetamide using KOH in glycol gives only a 62% yield of the amine after heating under reflux for 2 days (J. Am. Chem. Soc. 70 (1948) 4048).

In all the processes hitherto known, although the t.-alkylamines can be obtained, the acid component is as a rule lost in the effluent. In addition, the procedure of carrying out the reaction in polar, high-boiling solvents such as glycol demands particular efforts in order to purify the effluent.

German Offenlegungsschrift [German Published Specification] 2,164,239 describes the alkaline scission of propionic acid N-t.-alkylamides and acrylic acid N-t.-alkylamides in NaOH or KOH in methanol or methanol/water mixtures as the reaction medium at temperatures of 150° to 250° C. The process has the disadvantage that the mixture of methanol, water and t.-butylamine which is produced in working up can only be worked up to give pure t.-butylamine by means of a high outlay on distillation and subsequently drying the amine. Similarly, the recovery of the methanol from the reaction mixture requires more effort.

The hydrolysis of thiobispropionic acid N-t.-butylamide using a 13% strength NaOH at 165° to 185° C. is described in Japanese Patent Application 50-95,210. Repetition of the experiment has shown, however, that not more than 70–75% of the t.-butylamine and 50% of the thiobispropionic acid can be isolated by this process. A far-reaching decomposition of the molecule takes place, which prevents the isolation of thiobispropionic acid at temperatures above 200° C.

It is also known from J. Am. Chem. Soc. 70 (1948), 4048 that N-tert.-alkylamides can be split, at elevated temperature, for example when distilled, into the nitrile on which they are based, an olefin and water.

On the basis of the facts described, it was surprising and could not have been foreseen that N-t.-alkylamides can be hydrolyzed to give the carboxylic acid on which they are based and the t.-alkylamine in a smooth reaction and with good yields at a temperature of at least 200° C., using an alkali metal hydroxide in water as the reaction medium.

A process has now been found for the simultaneous preparation of carboxylic acids and N-tert.-alkylamines, which is characterized in that a carboxylic acid N-t.-alkylamide of the formula

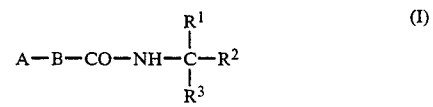

in which

A represents an optionally substituted phenyl, naphthyl or pyridyl radical or the aliphatic radical

wherein $R^4$, $R^5$ and $R^6$ are identical or different and independently of one another denote hydrogen or straight-chain or branched alkyl groups having 1 to 8 carbon atoms, it being also possible for $R^4$ and $R^5$ together to form an aliphatic ring e.g. cycloalkyl ring, having 4 to 8 ring members, B represents a single carbon bond, an aliphatic radical, e.g. alkyl, alkenyl radical, having 1 to 6 carbon atoms or a cycloaliphatic radical, e.g. cycloalkyl radical, having 4 to 8 carbon atoms, it being possible for each carbon atoms, independently of the others, to be substituted by straight-chain or branched $C_1$-$C_4$-alkyl groups, and $R^1$, $R^2$ and $R^3$ are identical or different and independently of one another denote straight-chain or branched alkyl groups having 1 to 8 carbon atoms, it being also possible for $R^1$ and $R^2$ together to form an aliphatic ring, e.g. cycloalkyl ring, having 4 to 8 ring members or for $R^1$ to be an optionally substituted phenyl radical.

is reacted at 200° to 350° C. under elevated pressure with 5 to 50% strength by weight aqueous alkali metal hydroxide in an amount of 1.0 to 1.3 mols per mol of the amide.

A preferably denotes an optionally substituted phenyl, naphthyl or pyridyl radical, particularly preferably an optionally substituted phenyl or naphthyl radical and very particularly preferably the optionally substituted phenyl radical.

B preferably denotes a single carbon bond or a $CH_2$ group which can be substituted by straight-chain and/or branched $C_1$-$C_4$-alkyl groups, particularly preferably a $CH_2$ group.

$R^1$, $R^2$ and $R^3$ preferably denote, independently of one another, the methyl or ethyl group.

Suitable substituents for the phenyl or naphthyl radical are halogen, such as fluorine, chlorine or bromine, preferably fluorine or chlorine, straight-chain or branched $C_1$-$C_6$-alkyl, preferably methyl or ethyl, $C_4$-$C_8$-cycloalkyl, preferably $C_5$-$C_6$-cycloalkyl, or phenyl.

Suitable substituents for the pyridyl radical are straight-chain or branched $C_1$-$C_6$-alkyl, preferably methyl or ethyl.

It follows from this that examples of carboxylic acid N-tert.-alkylamides which can be employed preferentially in the process according to the invention are those of the formula

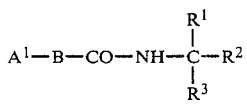

(II)

in which $A^1$ denotes the optionally substituted phenyl, naphthyl or pyridyl radical and B, $R^1$, $R^2$ and $R^3$ have the meaning indicated above.

Further carboxylic acid N-tert.-alkylamides which can be employed preferentially are those of the formula

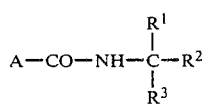

(III)

in which

A, $R^1$, $R^2$ and $R^3$ have the meaning indicated above.

Carboxylic acid N-tert.-alkylamides which can be employed particularly preferentially are those of the formula

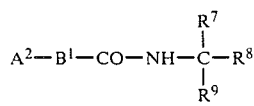

(IV)

in which $A^2$ denotes the optionally substituted phenyl radical, $B^1$ denotes a single carbon bond or a $CH_2$ group which can be substituted by straight-chain and/or branched $C_1$-$C_4$-alkyl groups, and $R^7$, $R^8$ and $R^9$ independently of one another denote methyl or ethyl.

Further carboxylic acid N-tert.-alkylamides which are particularly preferred are those of the formula

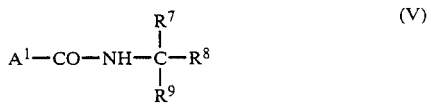

(V)

in which $A^1$, $R^7$, $R^8$ and $R^9$ have the meaning indicated above.

Carboxylic acid N-tert.-alkylamides which are very particularly preferred are those of the formula

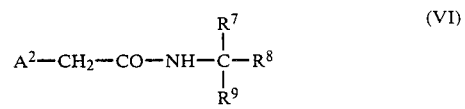

(VI)

in which $A^2$, $R^7$, $R^8$ and $R^9$ have the abovementioned meaning.

Phenylacetic acid N-tert.-butylamide may be mentioned as an example under formula (VI).

The N-t.-alkylamides which can be employed in accordance with the invention are known or can be prepared by the reaction known as the Ritter reaction from the carboxylic acid nitriles by means of tert.-alcohols, t.-alkyl ethers, t.-alkyl esters or olefines in the presence of strong acids (Houben-Weyl, Methoden der organischen Chemie [Methods of Organic Chemistry], volume 11/1, pages 994 to 1000 (1957); Organic Reactions, volume 17, pages 215 to 324; and Russian Chemical Review 29, 334 (1960)). They are therefore described as Ritter amides in the following text.

Examples of alkali metal hydroxides which may be mentioned are the hydroxides of all the metals of the first main group of the periodic system (Mendeleev) but preferably sodium hydroxide or potassium hydroxide. The alkali metal hydroxide is employed in the form of a 5 to 50% strength by weight aqueous solution, preferably a 10 to 35% strength by weight aqueous solution.

1.0 to 1.3 mols, preferably 1.0 to 1.15 and particularly preferably 1.0 to 1.05 mols, per mol of the amide, should be mentioned as an example of the quantity of alkali metal hydroxide. It is, of course, also possible to hydrolyze the Ritter amide using quantities of alkali metal hydroxide outside the ranges mentioned. However, quantities smaller than those mentioned make it necessary to separate off unreacted starting material, while quantities larger than those indicated increase to an unnecessary extent the burden of salt in the workingup process.

The process according to the invention is carried out at a temperature of about 200° to 350° C., preferably 230° to 350° C. and particularly preferably 255° to 350° C. and under a pressure of, for example, 10 to 200 bar, depending on the variable level of reaction temperature selected. The pressure under which the reaction takes place is essentially the autogenous pressure of the component water and the component t.-alkylamine in the reaction mixture. In addition, it is possible to inject an extraneous pressure by means of an inert gas, such as $N_2$, $H_2$, $CH_4$ or noble gases. This additional pressure is, however, not fundamental to the invention. It is preferable to work under the autogenous pressure of the reaction system at the reaction temperature employed.

The process according to the invention can be carried out, for example, by mixing the Ritter amide in the form of a solid or a melt with the alkali metal hydroxide solution at a temperature between room temperature and the reaction temperature. This mixing process can be carried out discontinuously or continuously and under normal pressure or under elevated pressure. The mixing process can be carried out in the pressure vessel for the reaction or in an upstream mixing vessel. The reaction mixture is then brought to the reaction temperature indicated and is kept at this temperature until the reaction is complete. The end of the reaction is evident from the fact, for example, that the pressure, which initially is still increasing, reaches a constant value. During the reaction, the mixture is vigorously stirred or is kept in constant agitation in a residence time system, so as to ensure continuous thorough mixing of all the reactants. In principle, the process according to the invention can be carried out discontinuously, for example in an autoclave or pressure kettle, or continuously, for example in a flow tube which can be heated and is resistant to pressure.

When the reaction is complete, the reaction mixture is cooled and the pressure is released. The t.-alkylamine is then removed from the reaction mixture by distillation. This removal by distillation can also be effected by controlled release of the pressure of the reaction mixture while the latter is still hot. This gives, if appropriate after a further distillation to remove water, a t.-alkylamine which has a purity higher than 97% in a yield of more than 95% of the theoretical yield. The t.-alkylamine obtained in accordance with the invention is free from ammonia.

Higher-boiling t.-alkylamines which cannot be removed from the reaction mixture by distillation are isolated from the reaction mixture, for example by extraction with a suitable extracting agent, and, after the removal of the extracting agent, are purified, for example by distillation.

The distillation bottom product or extracted water phase which remains is an aqueous alkaline solution of the sodium or potassium salt of the carboxylic acid. After neutralization, this solution can be purified from small residues of unreacted starting product or by-products, for example by filtration or extraction with an organic solvent. As a rule, however, this solution can be used directly for further purposes after the content of carboxylic acid salt has been adjusted to the desired value by concentration or dilution.

The free carboxylic acid can also be isolated from the solutions thus obtained, by customary methods, for example by acidifying the aqueous phase and removing the precipitated acid by filtration or extraction. This will be described in greater detail using as an example phenylacetic acid N-t.-butylamide:

Reacting phenylacetic acid N-t.-butylamide with, for example, aqueous 15% strength sodium hydroxide solution or 35% strength potassium hydroxide solution at temperatures of, for example, 230° to 280° C. gives a homogeneous reaction mixture from which t.-butylamine can be isolated by distillation in a high state of purity and in a yield of more than 95%.

After appropriate concentration by distilling off water, the distillation bottom product which remains constitutes a saturated solution of sodium phenylacetate or potassium phenylacetate.

The 10 to 60% strength solutions of the alkali metal salts, particularly the potassium salts, of phenylacetic acid produced in the process according to the invention are used, for example, in the preparation of penicillin G by fermentation (Ullmanns Enzyklopädie der technischen Chemie [Ullmann's Encyclopaedia of Industrial Chemistry], 4th edition, 1976, volume 11, pages 71 to 72).

t.-Butylamine finds applications in many fields. Thus French No. 1,513,261 describes t.-butylamine as an essential constituent of fungicidal mixtures. German Offenlegungsschrift [German Published Specification] 2,006,830 describes the reaction of 1 mol of dimethylamine and 1 mol of t.-butylamine in the presence of aqueous NaOH and hexane at 15° to 30° C. with 2 mols of sulphur monochloride to give a rubber vulcanisation agent. U.S. Pat. No. 3,416,604 describes the use of t.-butylamine as a crosslinking component for epoxide resins, and French No. 1,507,885 describes the use of t.-butylamine for the preparation of cellulose acetate membranes.

The examples mentioned in the following text are intended to describe the process in greater detail, but not to limit it to the examples mentioned.

EXAMPLE 1

191.3 g (1 mol) of N-t.-butyl-phenylacetamide and 300 g of 15% strength NaOH (1.125 mols) are heated at 260° C. with vigorous stirring in a 0.7 liter nickel autoclave. A constant pressure of 53 bar has been set up after 5 hours. The autoclave is cooled and the contents are run into a distillation apparatus. Distillation through a 30 cm column up to a head temperature of 100° C. gives 73.4 g of t.-butylamine of 97.3% purity. The yield is 97.7% of the theoretical yield. The t.-butylamine is free from ammonia.

The bottom product from the distillation (417 g) contains 32.5% by weight of phenylacetic acid (potentiometric titration after ion exchange) in the form of the sodium salt, corresponding to 99.5% of the theoretical yield.

The free phenylacetic acid is isolated by acidifying the distillation bottom product with 300 ml of 15% strength hydrochloric acid, filtering off with suction the colourless, crystalline product which is precipitated, washing it with 200 ml of water and drying it in vacuo at 50° C.

131.7 g of 97.5% strength phenylacetic acid of melting point 76° C. (literature melting point 78° C.) are obtained, corresponding to a yield of 94.3% of the theoretical yield.

EXAMPLES 2–10

Examples 2–10 were carried out analogously to Example 1; their reaction parameters and yields are listed in Table 1.

TABLE 1

Alkaline pressure hydrolysis of N—t.-butyl-phenylacetamide (1 mol)

| Example No. | Mols of alkali | Concentration of the alkali (%) | Reaction temperature (°C.) | Reaction time (hours) | Pressure bar | Phenylacetic acid Weight of the solution (g) | Content of free acid % | % of theoretical yield | t.-butylamine Weight of the distillate | Purity (%) | % of theoretical yield |
|---|---|---|---|---|---|---|---|---|---|---|---|
| 2 | 1.10 mols of NaOH | 14.5 | 260 | 3.0 | 51 | 418 | 32.2 | 99.0 | 75.0 | 95.6 | 98.0 |
| 3 | 1.00 mol of NaOH | 13.3 | 260 | 4.5 | 53 | 416 | 32.4 | 99.0 | 73.1 | 96.2 | 96.2 |
| 4 | 1.10 mols of KOH | 19.2 | 260 | 10 | 43 | 436 | 31.0 | 99.3[1] | 73.7 | 96.4 | 97.1 |
| 5 | 1.00 mol of KOH | 17.75 | 260 | 13 | 79 | 432 | 31.2 | 98.9[1] | 72.1 | 97.1 | 96.1 |
| 6 | 1.05 mols of NaOH | 30.0 | 250 | 5 | 49 | 446[2] | 30.3 | 99.4 | 73.6 | 95.5 | 97.3 |
| 7 | 1.05 mols of NaOH | 48.0 | 250 | 5 | 47 | 405[2] | 32.5 | 97.0 | 73.5 | 96.4 | 97.0 |
| 8 | 1.10 mols of NaOH | 15.0 | 230 | 3 | 43 | 437 | 30.7 | 98.7 | 74.3 | 96.7 | 98.4 |
| 9 | 1.10 mols of KOH | 35.0 | 230 | 7 | 43 | 298 | 45.2 | 99.1[1] | 73.4 | 97.5 | 98.1 |
| 10 | 1.10 mols of KOH | 35.0 | 210 | 20 | 31 | 303 | 43.6 | 97.2[1] | 73.2 | 97.1 | 97.3 |

[1] The K salt solutions can be used without intermediate isolation for the synthesis of penicillin.
[2] After adding 200 g of water

EXAMPLE 11

(Comparison example according to Japanese Patent Application No. 50-95,210)

145 g (0.5 mol) of N,N-di-t.-butyl-thiobispropionamide and 347 g of 15% strength NaOH (1.3 mols) are stirred vigorously for 5 hours at 180° C. in a 0.7 l nickel autoclave. The reaction mixture is cooled and run into a distillation apparatus. The amine is removed by distillation up to a head temperature of 100° C. 55.5 g of t.-butylamine of 97.3% purity are obtained.

Yield: 74% of the theoretical yield.

The pH of the distillation bottom product is adjusted to 1 with 30% strength hydrochloric acid. In the course of this large quantities of hydrogen sulphide are evolved from the reaction mixture. The carboxylic acid which has been precipitated is filtered off with suction, washed with 100 ml of water and dried. 53.3 g of thiobispropionic acid of 83% purity are obtained.

Yield: 49.7% of the theoretical yield.

EXAMPLE 12

225.5 g (1 mol) of N-t.-butyl-(2-chlorophenyl)-acetamide (melting point: 128°-130° C.) and 281 g of 15% strength NaOH (1.05 mols) are heated at 260° C., while stirring, for 3 hours in a 0.7 l nickel autoclave. The autoclave is cooled and the reaction mixture is run into a distillation apparatus. Distillation through a 30 cm column up to a head temperature of 100° C. gives 71.5 g of t.-butylamine of 97% purity, corresponding to a yield of 95% of the theoretical yield. 200 ml of water and 100 ml of 30% strength hydrochloric acid are added to the distillation bottom product. The acid which has been precipitated is filtered off with suction and dried in vacuo. 157.8 g of o-chlorophenylacetic acid of melting point 95° C. are obtained.

Yield: 92% of the theoretical yield.

EXAMPLE 13

260 g (1 mol) of N-t.-butyl-(2,4-dichlorophenyl)-acetamide (melting point: 111°-113° C.) are reacted analogously to Example 12 with 281 g of 15% strength NaOH (1.05 mols) at 250°. After distillation, 72.8 g of t.-butylamine of 97.8% purity are obtained, corresponding to a yield of 97.3%.

182.2 g of 2,4-dichlorophenyl acetic acid of melting point 116°-118° C. are obtained by acidifying the distillation bottom product.

Yield: 89% of the theoretical yield.

EXAMPLE 14

205 g (1 mol) of N-t.-pentyl-phenylacetamide (melting point: 96° C.) are stirred with 293 g of 15% strength NaOH (1.1 mols) for 5 hours at 255° C., analogously to Example 12. After distillation, 85.2 g of t.-pentylamine of 97% purity are obtained, corresponding to a yield of 95%.

123 g of phenylacetic acid are obtained by acidifying the distillation bottom product.

Yield 90.4%.

EXAMPLE 15

191.2 g (1 mol) of N-t.-butyl-p-methylbenzamide (melting point: 113°-115° C.) are stirred with 281 g of 15% strength NaOH (1.05 mols) for five hours at 250° C. The reaction mixture is run into a distillation apparatus and the amine is removed by distillation through a column: 72 g of t.-butylamine of 97.4% purity are obtained, corresponding to a yield of 96%.

The distillation bottom product is acidified with 130 ml of 30% strength hydrochloric acid and the product which has been precipitated is filtered off with suction and dried. 124.2 g of p-toluic acid of melting point 178°-179° are obtained.

Yield: 91.3%.

EXAMPLE 16

158.6 g (0.75 mol) of o-chlorobenzoic acid N-t.-butylamide (melting point: 104°-105° C.) and 220 g of 15% strength NaOH (0.825 mol) are heated at 280° C. for ten hours while stirring vigorously. The reaction mixture is run into a distillation apparatus and the amine is removed by distillation. 50.5 g of t.-butylamine of 97.1% purity are obtained. The pH of the distillation bottom product is adjusted to 7 with 10% strength hydrochloric acid and the precipitate is filtered off with suction and washed with 100 ml of water. After drying, 10.6 g of residual o-chlorobenzoic acid N-t.-butylamide are obtained. This means a conversion of 93.3%.

The neutral mother liquor and the wash water are combined and adjusted to pH=1 with 100 ml of 30% strength hydrochloric acid. The acid which has been precipitated is filtered off with suction and dried. 95.4 g of o-chlorobenzoic acid of melting point 136°–138° C. are obtained.

Yield: 86%.

EXAMPLE 17

191.0 g (1 mol) of benzoic acid N-t.-pentylamide and 281 g of 15% strength NaOH (1.05 mols) are heated at 250° C. for 4 hours while stirring. Working up as in Example 15 gives 86.6 g of t.-pentylamine of 97.2% purity, corresponding to a yield of 96.7%, and 116 g of benzoic acid, corresponding to a yield of 95%.

EXAMPLE 18

227 g (1 mol) of α-naphthoic acid N-t.-butylamide (melting point: 144°–146° C.) are stirred vigorously with 293 g of 15% strength NaOH (1.10 mols) for 10 hours at 280° C. The reaction mixture is cooled and transferred to a distillation apparatus, and the amine is removed by distillation until a bottom temperature of 105° C. is reached. 71.6 g of t.-butylamine of 98.2% purity are obtained.

Yield: 96.3%.

The pH of the distillation bottom product is adjusted to 1 and the acid which has been precipitated is isolated and dried. 160 g of α-naphthoic acid of melting point 162°–163° are obtained.

Yield: 92.9%.

EXAMPLE 19

178.1 g (1 mol) of isonicotinic acid N-t.-butylamide (melting point 119°–123°) are stirred with 266 g of 15% strength sodium hydroxide solution (1 mol) for 4 hours at 260° C. A pressure of 45 bar is set up. The amine is removed by distillation from the reaction mixture until the head temperature reaches 100° C. 71.5 g of t.-butylamine of 97% purity are obtained.

Yield 95%.

The pH of the distillation bottom product is adjusted to 3 and the acid which has been precipitated is filtered off with suction, washed with 100 ml of water and dried. 112 g of isonicotinic acid of melting point >300° C. are obtained.

Yield: 91%.

EXAMPLE 20

178.1 g (1 mol) of N-t.-butyl-picolinamide (boiling point/10:150° C.) are stirred with 293 g of 15% strength NaOH (1.1 mols) for two hours at 250° C., and the product is worked up as in Example 19. 71.7 g of t.-butylamine of 97.4% purity are obtained.

Yield: 95.6%.

The pH of the distillation bottom product is adjusted to 3 with 30% strength hydrochloric acid, and the acid which has been precipitated is filtered off with suction and dried. 108 g of picolinic acid of melting point 134°–136° C. are obtained.

Yield: 88%.

What is claimed is:

1. A process for the simultaneous preparation of a carboxylic acid and N-tert.-alkylamine which comprises contacting a carboxylic acid N-tert.-alkylamide of the formula

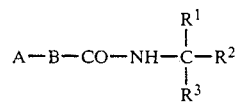

wherein:
A represents an optionally substituted phenyl naphthyl or pyridyl radical;
B represents a single carbon bond, an aliphatic radical having 1 to 6 carbon atoms or a cycloaliphatic radical having 4 to 8 carbon atoms, it being possible for each carbon atom, independently of the others, to be substituted by a straight-chain or branched $C_1$–$C_4$-alkyl group, and
$R^1$, $R^2$ and $R^3$ are identical or different and independently of one another denote a straight-chain or branched alkyl group having 1 to 8 carbon atoms, it also being possible for $R^1$ and $R^2$ together to form an aliphatic ring, e.g. cyclo alkyl ring, having 4 to 8 ring members, or for $R^1$ to be an optionally substituted phenyl radical,
with a 5 to 50% strength by weight aqueous alkali metal hydroxide at 200° to 350° C. under elevated pressure while employing 1.0 to 1.3 mols of alkali metal hydroxide per mol of said carboxylic acid N-tert.-alkylamide, the reaction mixture consisting essentially of water, said aqueous alkali metal hydroxide and said N-tert.-alkylamide.

2. A process according to claim 1, wherein said carboxylic acid N-tert.-alkylamide is one of the formula

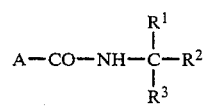

wherein:
A, $R^1$, $R^2$ and $R^3$ have the meaning given in claim 1.

3. A process according to claim 1, wherein:
A denotes an optionally substituted phenyl radical,
B denotes a single carbon bond or a $CH_2$ group which can be substituted by a straight chain or branched $C_1$–$C_4$-alkyl group, and
$R^1$, $R^2$ and $R^3$ independently of one another denote methyl or ethyl.

4. A process according to claim 1, wherein a 10 to 35% strength by weight alkali metal hydroxide is employed.

5. A process according to claim 1, wherein 1.0 to 1.15 mols of alkali metal hydroxide are employed per mol of amide.

6. A process according to claim 1, wherein 1.0 to 1.05 mols of alkali metal hydroxide are employed per mol of amide.

7. A process according to claim 1, wherein the process is carried out at a temperature of 230° to 350° C.

8. A process according to claim 1, wherein the process is carried out at a temperature of 255° to 350° C.

9. A process according to claim 1, wherein the process is carried out in a closed vessel under autogenous pressure.

10. A process according to claim 1, wherein said amide is N-tert.-butyl-phenylacetamide.

11. A process according to claim 1, wherein said amide is N-tert.-butyl-(2-chlorophenyl)acetamide.

12. A process according to claim 1, wherein said amide is N-tert.-butyl-(2,4-dichlorophenyl)acetamide.

13. A process according to claim 1, wherein said amide is N-tert.-pentyl-phenylacetamide.

14. A process according to claim 1, wherein said amide is N-tert.-butyl-p-methybenzamide.

15. A process according to claim 1, wherein said amide is o-chlorobenzoic acid N-tert.-butylamide.

16. A process according to claim 1, wherein said amide is benzoic acid N-tert.-pentylamide.

17. A process according to claim 1, wherein said amide is α-naphthoic acid N-tert.-butylamide.

18. A process according to claim 1, wherein said amide is isonicotinic acid N-tert.-butylamide.

19. A process according to claim 1, wherein said amide is N-tert.-butyl-picolinamide.

* * * * *